United States Patent [19]
Shiber

[11] Patent Number: 4,886,490
[45] Date of Patent: Dec. 12, 1989

[54] ATHERECTOMY CATHETER SYSTEM AND METHOD OF USING THE SAME

[75] Inventor: Samuel Shiber, Mundelein, Ill.

[73] Assignee: Surgical Systems & Instruments, Inc., Mundelein, Ill.

[21] Appl. No.: 243,900

[22] Filed: Sep. 13, 1988

Related U.S. Application Data

[63] Continuation-in-part of Ser. No. 078,042, Jul. 27, 1987, Ser. No. 205,479, Jun. 13, 1988, and Ser. No. 225,880, Jul. 29, 1988, each is a continuation-in-part of Ser. No. 874,546, Jun. 16, 1986, Pat. No. 4,732,154, which is a continuation-in-part of Ser. No. 609,846, May 14, 1984, abandoned.

[51] Int. Cl.⁴ ............................................. A61B 17/32
[52] U.S. Cl. ..................................... 604/22; 128/305
[58] Field of Search ............... 128/305, 304, 753, 754; 604/22

[56] References Cited

U.S. PATENT DOCUMENTS 4,445,509  5/1984  Auth .................................... 128/305
4,627,436  12/1986  Leckrone ......................... 128/303.1

FOREIGN PATENT DOCUMENTS

163502  12/1985  European Pat. Off. ............ 128/305
2804015  8/1979  Fed. Rep. of Germany ...... 128/305

Primary Examiner—Michael H. Thaler
Attorney, Agent, or Firm—Samuel Shiber

[57] ABSTRACT

An atherectomy system for coring, ingesting and removing an obstruction from within a patient's vessel, comprising a flexible guide-wire insertable into the vessel, a flexible rotary-catheter being rotatably disposed and insertable into the vessel over the flexible guide-wire, having a rotary coring device, at its distal end for making a peripheral cut in an obstruction located in front of it, relative motion between the flexible rotary-catheter and the flexible guide-wire is used to mechanically enable the ingested obstruction material to proximally move into the flexible rotary-catheter.

28 Claims, 7 Drawing Sheets

ATHERECTOMY CATHETER SYSTEM AND METHOD OF USING THE SAME

CROSS REFERENCE TO OTHER APPLICATIONS AND BACKGROUND OF THE INVENTION

This application is a continuation in part (CIP) of three applications: Application Ser. No. 078,042 filed 7/27/87, Application Ser. No. 205,479 filed 6/13/1988 and application 225,880 filed 7/29/88. These three applications are CIPs of application Ser. No. 018,083 filed 2/24/1987, which is a CIP of application Ser. No. 874,546 filed 6/16/1986 (now patent 4,732,154) which is a CIP of application Ser. No. 06/609,846 filed 5/14/1984 (abandoned).

All above prior applications are hereby being incorporated by reference.

With age a large percentage of the population develops atherosclerotic arterial obstructions resulting in a diminished blood circulation. The disturbance to blood flow that these obstructions cause may induce blood clots which further diminish or block the blood flow. When this process occurs in the coronary arteries it is referred to as a heart attack. Presently such obstructions are circumvented by surgically grafting a bypass or they are treated by a catheter equipped with a balloon which is inserted through the arterial system, over a flexible guide-wire, into the obstruction and then inflated to expand the obstruction's lumen (angioplasty). Some of the problems with angioplasty are that it injures the arterial wall, it creates a rough lumen and in substantial number of the cases it is ineffective. Further, angioplasty does not remove the obstruction material out of the arterial system, therefore in a case of a heart attack, immediate angioplasty carries the risk of dislodging the blood clot and allowing it to move down stream creating additional blockages.

An objective of the present invention is to provide an atherectomy catheter rotatable over a flexible guide-wire, equipped with a rotary coring means at its distal end, that would core and extract the obstruction material, including blood clots if present, create a smooth lumen and not crack the arterial wall. The design of an atherectomy catheter should lend itself to be producable in diameters down to around 1 mm (millimeter) and a length of up to a meter to enable it to reach and enter small and remote arteries.

Preferably, the operation of the atherectomy system would resemble the operation of present catheter systems, so that existing skills of the medical staff can be utilized. These and other objectives of the invention will become apparent from the following discussion and the accompanying drawings.

BRIEF DESCRIPTION OF THE FIGURES

FIG. 5' shows a cross sectioned view of the distal end portion of an atherectomy system utilizing the flexible guide-wire having triple windings. The flexible rotary-catheter is formed of a helical winding with a wire having a triangular cross section which provides a helical step.

DETAILED DESCRIPTION OF THE DRAWINGS

Figure 1:
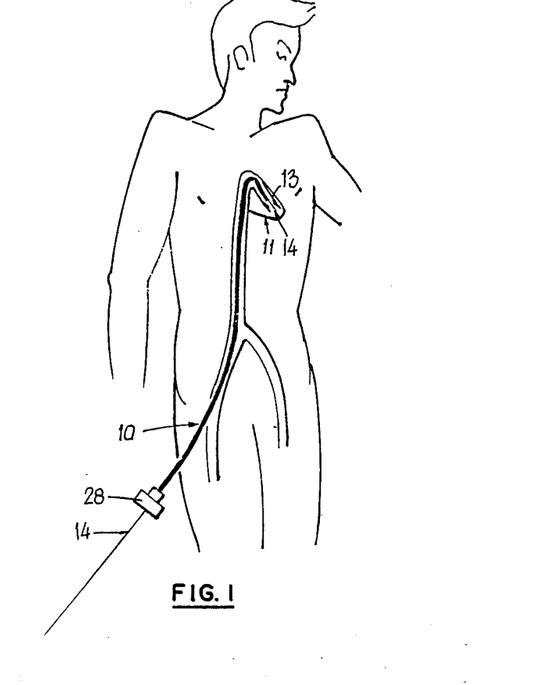
FIG. 1 generally shows an atherectomy system inserted at the groin area through the arterial system of a patient, into his coronary artery.

FIG. 1 generally shows an atherectomy system 10 inserted at the groin area, through a patient's arterial system into a coronary artery 13 serving the patient's heart 11.

Figure 2:
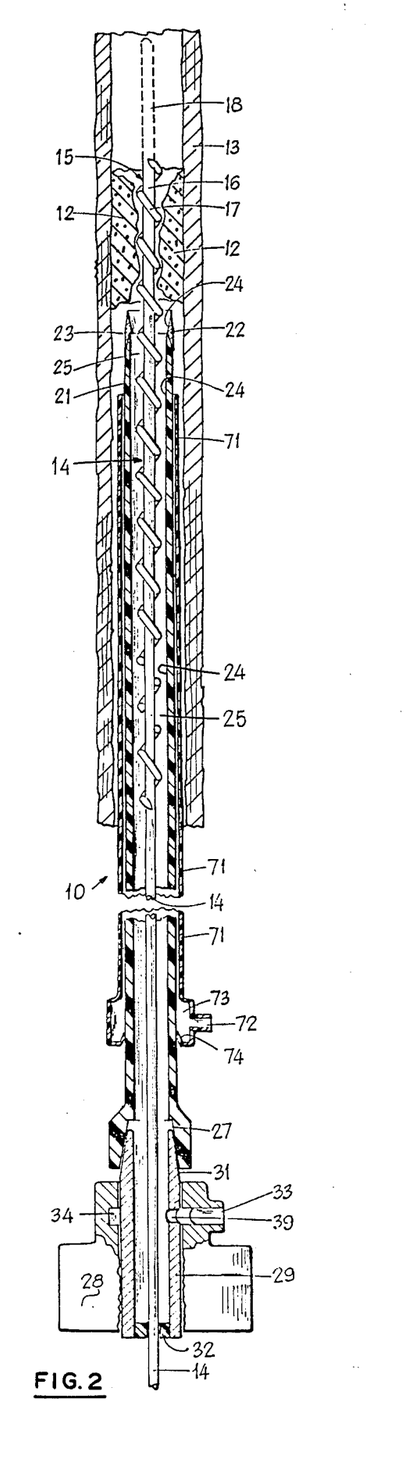
FIG. 2 shows a cross sectioned view of an atherectomy system. The middle portion of the atherectomy system is removed due to space limitations on the drawing sheet.

FIG. 2 shows the atherectomy system 10 (similar parts will be indicated by same numbers throughout the FIGURES) for coring ingesting and removing an obstruction 12 from within a patient's vessel 13. As shown in FIG. 2, the atherectomy system comprises several elongated parts in a nested relationship, and their ends shall be referred to as "distal" meaning the end which goes into the vessel and "proximal" meaning the other end. In view of the above, "distal direction" or the term "distally" shall indicate a general direction from the proximal end to the distal end, and "proximal direction" or "proximally" shall refer to an opposite direction.

The atherectomy system comprises:

A flexible guide-wire 14 which is insertable into the vessel. The distal end portion of the flexible guide-wire is shaped as an auger 15, made of a core wire 16 and a wire 17 which is helically wound around the core wire. At the distal tip the core wire is tapered and covered with a soft spring to form a standard guide-wire's tip 18.

A flexible rotary-catheter 21 is rotatably disposed and insertable into the vessel, over the flexible guide-wire.

A rotary coring means in the form of a tubular-blade 22, is located at the distal end of the flexible rotary-catheter. The term "rotary coring means" as used herein, means a tubular-blade with at least a part of its front edge being sharp, or a heated blade, or a radiation emitting means such as an optical fiber (or fibers) located at a wall of the flexible rotary-catheter carrying laser energy, or other means which core by making a narrow peripheral cut in an obstruction placed in front of it. The tubular-blade has an outer wall 23 which slidingly and rotatably bears against the arterial wall spreading the contact force on a relatively large area and thereby minimizing the damage to the artery. A rotary coring means is efficient and uses less energy in comparison to other systems which pulverize the mass of the material of the obstruction. To illustrate this point, when a tubular-blade cores and extracts an obstruction with an outside diameter of 3 mm, an inside diameter (lumen) of 1 mm and a length of 10 mm the area that the tubular-blade has to cut through is 94.25 square mm. If a pulverizing blade, for example as shown in U.S. Pat. No. 4,445,509 by Auth, is used to break the same obstruction to particles measuring 0.01 mm by 0.01 mm by 0.01 mm the area that a pulverizing blade would have had to cut through is 37,699 square mm, and this area which is 400 times larger requires a much larger energy input to the blade, thereby substantially increasing the probability of traumatizing the artery.

A rotating inner-wall 24 is formed by the inside surfaces of the rotary coring means and the flexible rotary-catheter.

A continuous passage 25 is defined between the rotating inner-wall and the flexible guide-wire, and the relative motion between the inner-wall and the flexible guide-wire mechanically acts on the ingested obstruction material in the continuous passage and enables it to move towards the proximal end of the flexible rotary-catheter and make room for additional cored material.

Coupling means at the proximal end of the flexible rotary-catheter in the form of a conical seat 27 couples it to rotating means in the form of a motor having a housing 28 and a hollow shaft 29 with a matching tapered end 31 and a seal 32 at its other end. The hollow shaft and seal are slidingly and rotatably disposed around the flexible guide-wire.

Suction can be applied to the flexible rotary-catheter through a port 33 which communicates through a groove 34, defined by the motor's housing, through hole 39 and through the hollow shaft to the proximal end of the continuous passage 25. The suction cooperates with the mechanical action taking place in the continuous passage in proximally moving the cored obstruction material.

Figure 4:
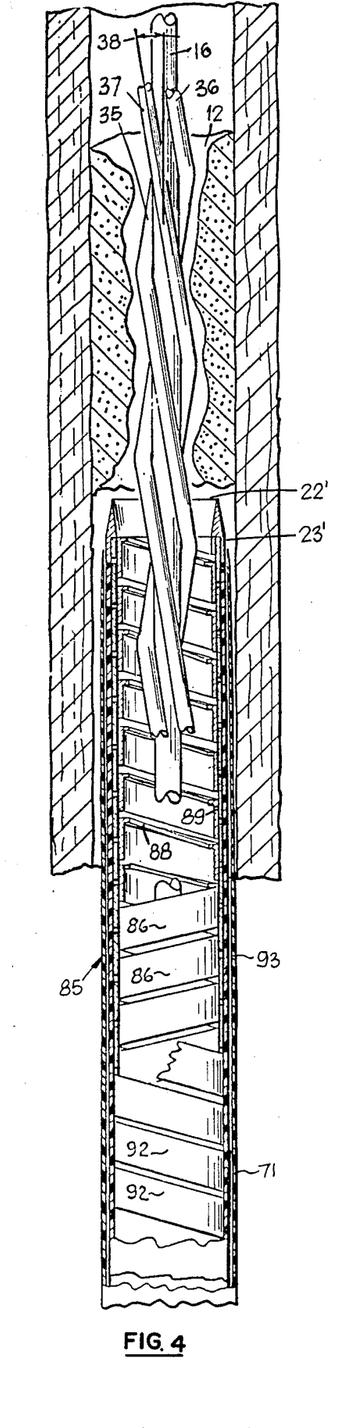
FIG. 4 shows a cross sectioned view of the distal end portion of an atherectomy system utilizing a flexible guide-wire having triple windings. The flexible rotary-catheter is formed of an outer helical winding wound over an inner helical winding which includes a radially protruding helical step. A plastic jacket coats the outer winding.
Figure 5:
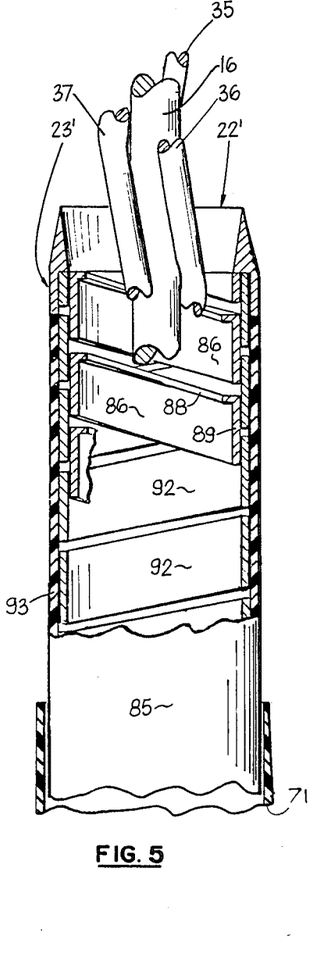
FIG. 5 is an enlarged cross sectioned view of the distal end of the system shown in FIG. 4.
Figure 6:
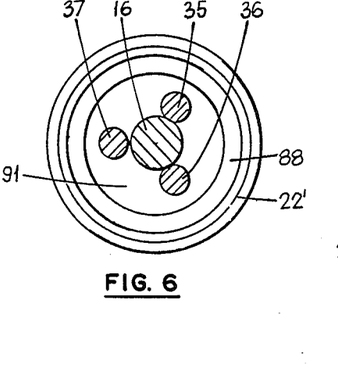
FIG. 6 shows a cross sectioned view of the distal end of the atherectomy systems shown in FIGS. 5 and 5'.

FIGS. 4, 5 and 6 show the distal end section of an atherectomy system having a flexible rotary-catheter 85 having an inner helical winding 86 with an inverted "L" cross section. The longer vertical part 89 forms a part of the inner-wall of the flexible rotary-catheter whereas the horizontal shorter part 88 extends radially into a continuous passage 91 to form the helical step 88 which mechanically acts on the cored material in the continuous passage pushing it in a proximal direction when the flexible rotary-catheter rotates forward ("forward rotation" of a part is defined herein as a clockwise rotation of the part when looking at its proximal end, "backward rotation" is an opposite rotation). The inner helical winding 86 tends to diametrically expand when the flexible rotary-catheter 85 is rotated forward by its proximal end, but this tendency is restrained by an outer helical winding 92, made of a flat ribbon and wound in a counter direction which tends to diametrically contract, acting as a hoop member balancing and restraining the inner winding's diametrical expansion. A jacket 93 made of plastic with a low coefficient of friction coats the outer windings. A tubular blade 22' attached to the distal end of the windings has a smooth outer surface 23' for slidingly bearing against an arterial wall while its sharp edge cores into an obstruction placed in front of it, and coupling means (not shown) is attached to the proximal end of the windings and has a conical seat for engaging the motor's shaft.

FIG. 5' shows an atherectomy system utilizing the same flexible guide-wire shown in FIG. 5. The flexible rotary-catheter 90 is formed of a helical winding 84 with a triangular wire cross section 101 which provides a protruding helical surface 100 to push the obstruction material into the flexible rotary-catheter as it rotates. The helical member is coated with a plastic layer forming a flexible tube 102. The flexible tube can extend distally to the blade, as shown in FIG. 5', alternatively the distal coils of the helical member 84 can be left bare to increase its flexibility and decrease its diameter or, the flexible tube 102 can be omitted all together. When the flexible tube is partially or completely missing the flexible rotary-catheter is not fluid worthy and in such cases a sleeve 87 can be distally extended to allow fluid conveyance and suction to reach the distal area of the atherectomy system. The sleeve 87 contains a helical reinforcement 94 to diametrically stabilize it as it is bent at the insertion point into the body (or into the artery in an intraoperative procedure) and elsewhere. Where the flexible tube is present it diametrically restrains the expansion of the helical member when torque is transmitted through it from the motor to the tubular blade.

The flexible guide-wire 14 shown in FIG. 2 (and is also shown in the embodiments shown in FIGS. 11, 13, 21, 23 and 25) does several things: It is a distal barrier countering distal movement of the obstruction material in the artery before and while it is being cored, it is an anti-rotational device which restrains the cored material from freely rotating around the flexible guide-wire and to the extent that the obstruction material does rotate around the flexible guide-wire this rotation is translated by the auger to proximally urge the cored obstruction material in the continuous passage. In addition when the flexible guide-wire has to be inserted into a tight obstruction the auger can be screwed into the obstruction by rotating the flexible guide-wire backwards.

Further, the auger guides the flexible rotary-catheter on the side of its wire 17, taking up the free play between the core wire 16 and the flexible rotary-catheter. If instead of an auger a conventional flexible guide-wire (with an outside diameter equal to the auger's outside diameter) was used, it would have made the system less effective and interfere with the ingestion of the cored obstruction material into the continuous passage, as discussed above.

The auger can be modified by varying its helix angle and/or the number of wires coiled around its core wire. FIGS. 4, 5, and 6 show a flexible guide-wire with three wires 35, 36 and 37, attached to a core wire 16. At an extreme case, when the helix angle 38 is zero degrees, the wires 35, 36 and 37 are parallel to the core wire, and the flexible guide-wire serves as an anti-rotational device but is not effective by itself as a distal barrier or in urging the cored obstruction material into the continuous passage. These functions are increased as the angle 38 is increased. Therefore, a flexible rotary-catheter that has means of pushing the cored obstruction material into the continuous passage, like the flexible rotary-catheter shown in FIG. 4, may be teamed with flexible guide-wires which function mostly as anti-rotational devices whereas a flexible rotary-catheter without such additional means are preferably teamed with a flexible guide-wire having a more pronounced helix angle.

Figure 7:
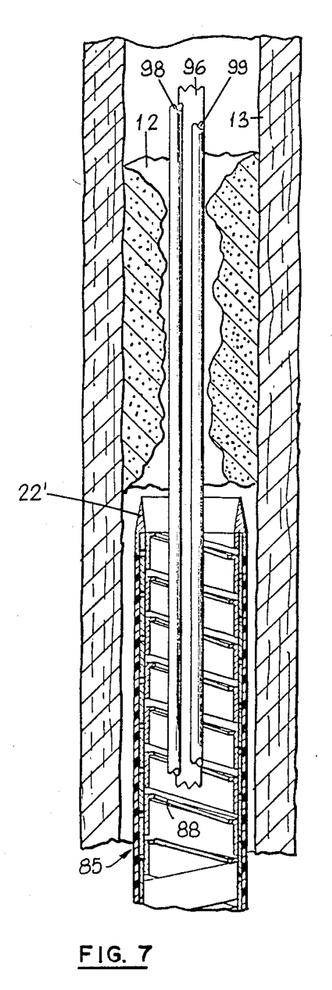
FIG. 7 shows a cross sectioned view of the distal end portion of the same flexible rotary-catheter shown in FIG. 4 over a hydraulically expandable flexible guide-wire, shown in its relaxed, contracted position.
Figure 8:
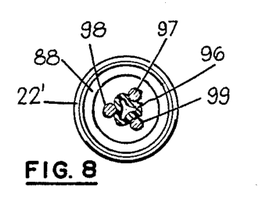
FIG. 8 shows a cross sectioned view of the flexible guide-wire shown in FIG. 7.
Figure 9:
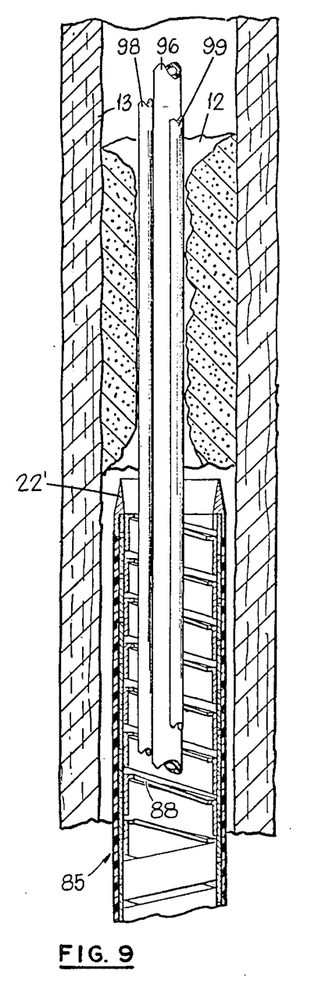
FIG. 9 shows a cross sectioned view of the distal end portion of the flexible rotary-catheter shown in FIG. 7 over the expandable flexible guide-wire, shown in its energized, expanded position.
Figure 10:
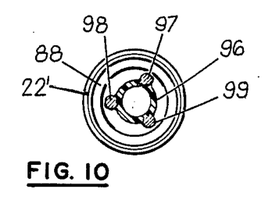
FIG. 10 shows a cross sectioned view of the expanded flexible guide-wire shown in FIG. 9.

FIGS. 7 to 10 show a flexible guide-wire having anti-rotational longitudinal ridges 97, 98 and 99, mounted onto a hydraulically expandable tube 96. In its relaxed position the tube has a clover leaf shape, harboring the elongated ridges as shown in FIGS. 7 and 8. The elongated tube is made of a non streching material and can be selectively, at its proximal end, inflated and expanded with fluid to become round as shown in FIGS. 9 and 10 thereby radially displacing the elongated ridges engaging into the obstruction material. As the flexible rotary-catheter 85 advances and rotates around the flexible guide-wire it cores, ingests and envelopes the obstruction's material. The helical step 88 utilizes the relative rotation to mechanically push the obstruction material into the continuous passage 91 while the ridges negate the material's rotation. When expanded the ridges move close to the helical step they provide positive guidance to the advancing flexible rotary-catheter.

Figure 11:
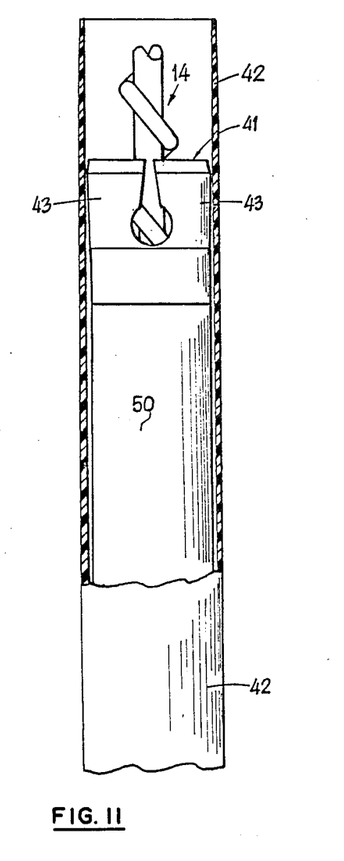
FIG. 11 shows the distal end portion of an atherectomy system having a rotary coring means in the form of a variable diameter tubular-blade, shown in its contracted position being compressed inside a sleeve.
Figure 12:
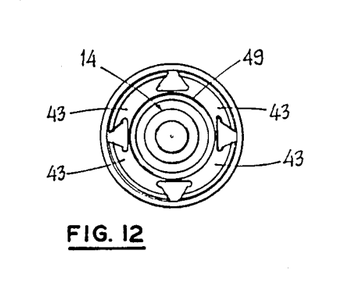
FIG. 12 shows the distal end of the variable diameter tubular-blade shown in FIG. 11.
Figure 13:
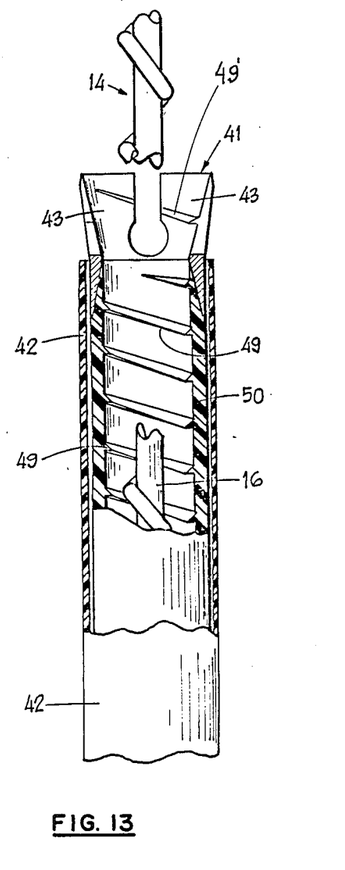
FIG. 13 shows a cross sectioned view of the variable diameter tubular-blade shown in FIG. 11 in its relaxed expanded position after it has emerged out of the sleeve. The variable diameter tubular-blade is mounted on a flexible rotary-catheter made of plastic with an integral helical step formed on its inner wall.
Figure 14:
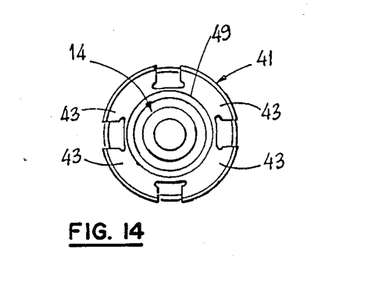
FIG. 14 shows the distal end of the variable diameter tubular-blade shown in FIG. 13.

FIGS. 11 and 12 show the rotary coring means being a variable diameter tubular-blade 41 in its contracted, compressed position as it is inserted into the vessel through a sleeve 42. The variable diameter tubular-blade (which resembles a collet of the type used in mechanical pencils to grip the lead) is made of four flexible leaves 43 which move radially to their relaxed position, shown in FIGS. 13 and 14 when they exit and are no longer compressed by the sleeve. This reduces the size of the initial puncture wound needed to introduce a certain size rotary coring means into an artery and thereby reduces the associated bleeding and other healing problems of the puncture wound. FIG. 13 also illustrates a helical step 49 and 49' formed on the inner-wall of the flexible rotary-catheter 50 which pushes the cored obstruction material proximally. Step 49 is formed on the flexible rotary-catheter portion of the inner wall and step 49' is formed on the tubular-blade portion of the inner wall.

Figure 15:
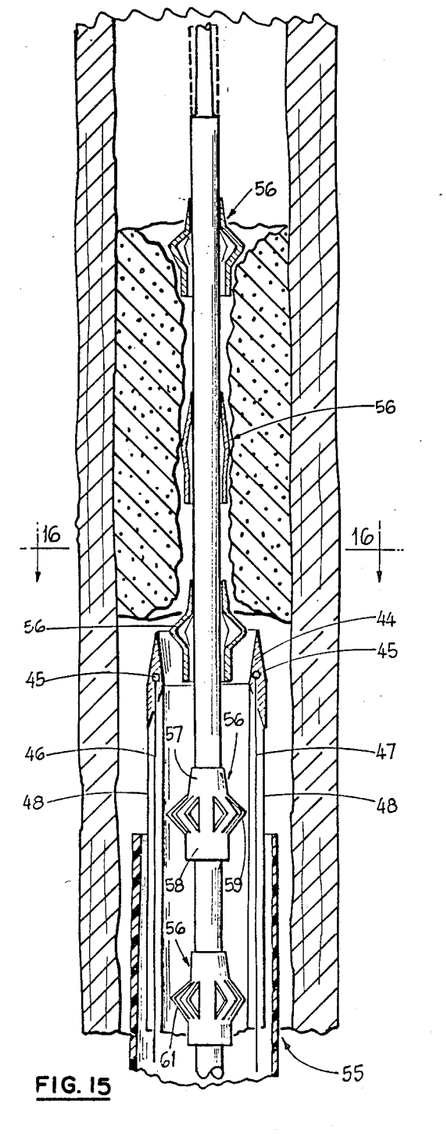
FIG. 15 shows a cross sectioned view of the distal end portion of an atherectomy system with a rotary coring means in the form of a heated tubular-blade, disposed over a flexible guide-wire having distal barrier devices resembling an umbrella mechanism.
Figure 16:
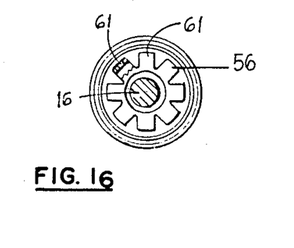
FIG. 16 shows a cross sectioned view of the system shown in FIG. 15 along a line 16—16 marked on FIG. 15.

FIG. 15 shows a distal end portion of an atherectomy system having a rotary coring means in the form of a heated tubular-blade 44 having a ring shaped heating element 45 to which energy is brought by means of two flexible conduits 46 and 47 embedded in a wall of a flexible rotary-catheter 48 (cross hatching omitted). The heating can be done electrically, in which case the conduits 46 and 47 are electrical wires and the heating element can be a resistive element, or the heating can be done with laser energy in which case the conduits 46 and 47 can be optical fibers and the heating element can serve to absorb the laser energy from the distal end of the optical fibers translating it to heat and distributing it to the tubular-blade 44. FIG. 15 further shows a flexible guide-wire which has a distal barrier means in the form of umbrella elements 56 to counter distal movement of surrounding obstruction material. The elements 56 can be made of thin plastic tube sections. They have a distal collar 57 affixed to the core wire 16 and a proximal collar 58 slidable on the core wire. These collars are connected to a slit collar 59. When the element 56 is pushed through a tight obstruction, the slit collar can elastically deform and close to the configuration that the second from the top element is illustrated in FIG. 15. Once it is past the obstruction the element 56 springs back and reopens. During the opening the collars 57 and 58 slide closer together and the arms of the slit collar 59 bend, like an umbrella's mechanism as the top element is illustrated in FIG. 15 and as shown in FIG. 16. In their open position the elements form a distal barrier and prevent the obstruction material from moving distally in the vessel and in the continuous passage while the flexible rotary-catheter cores and ingests the obstruction material.

Figures 17, 19:
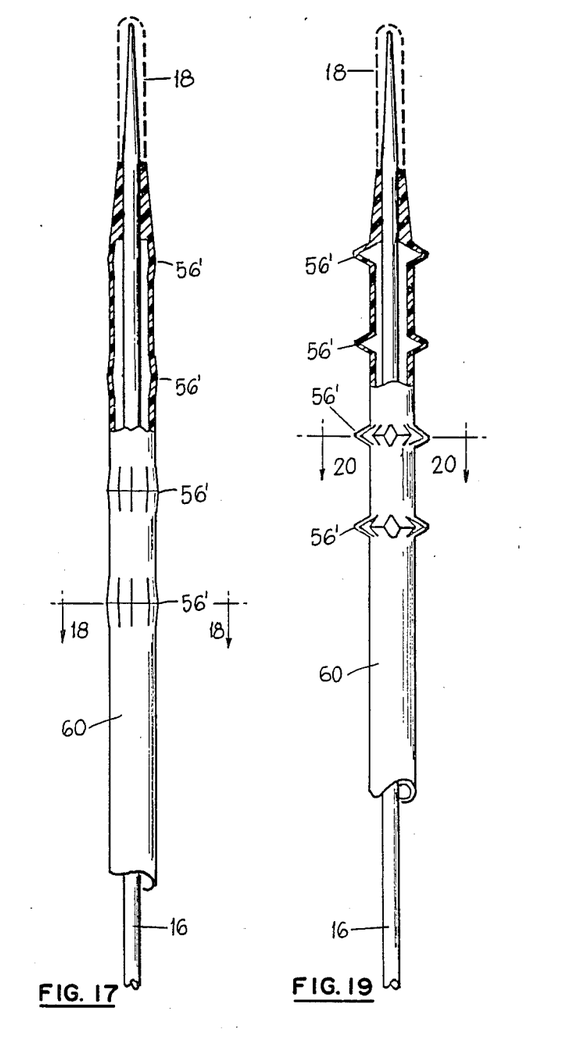
FIG. 17 shows a flexible guide-wire having selectively actuatable distal barrier devices resembling an umbrella mechanism in their closed position.
FIG. 19 shows the flexible guide-wire shown in FIG. 17 with the distal barrier devices in their expanded position.
Figure 18:
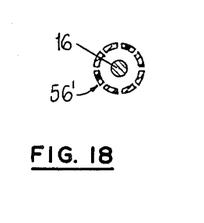
FIG. 18 shows a cross sectioned view of the flexible guide-wire shown in FIG. 17 along a line 18—18 marked on FIG. 17.
Figure 20:
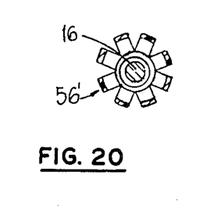
FIG. 20 shows a cross sectioned view of the flexible guide-wire shown in FIG. 19 along a line 20—20 marked on FIG. 19.

FIGS. 17 to 20 show selectively controlled distal barrier means formed by making several slits as shown, in a thin tube 60 thereby forming several umbrella elements 56' as an integral part of the thin tube. The distal end to the thin tube is bonded to the distal end of a core wire 16. The distal barrier means can be selectively expanded, as shown in FIGS. 19 and 20, and contracted, as shown in FIGS. 17 and 18, by pushing and pulling, respectively, the proximal end of the thin tube 60 while holding the proximal end of the core wire fixed in place.

Figure 21:
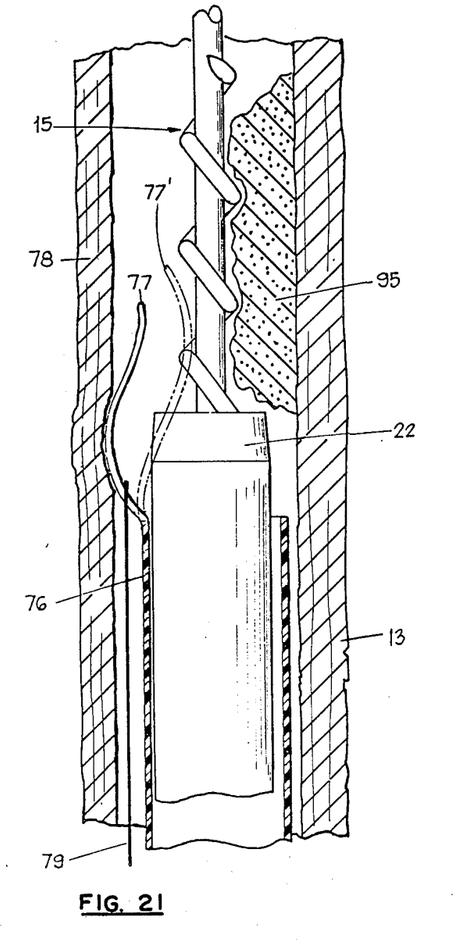
FIG. 21 shows a cross sectioned view of an atherectomy system with a flexible sleeve having a selectively actuatable tongue at its distal end.
Figure 22:
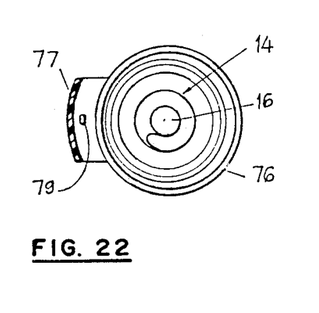
FIG. 22 shows a cross sectioned view of the tongue shown in FIG. 21.

FIGS. 21 and 22 show an atherectomy system where a flexible sleeve 76 has a tongue 77 which can be used when coring an eccentric obstruction 95. In such cases the tongue can be inserted opposite of the obstruction 95 to protect an arterial wall 78 and bias the rotary coring means into the obstruction. To further bias the flexible sleeve and the rotary coring means the tongue can be energized against the arterial wall by tensioning a flexible rope 79, moving the tongue from its relaxed position shown in a phantom line in FIG. 14 and marked 77' to the position shown in solid lines and marked 77.

Figure 23:
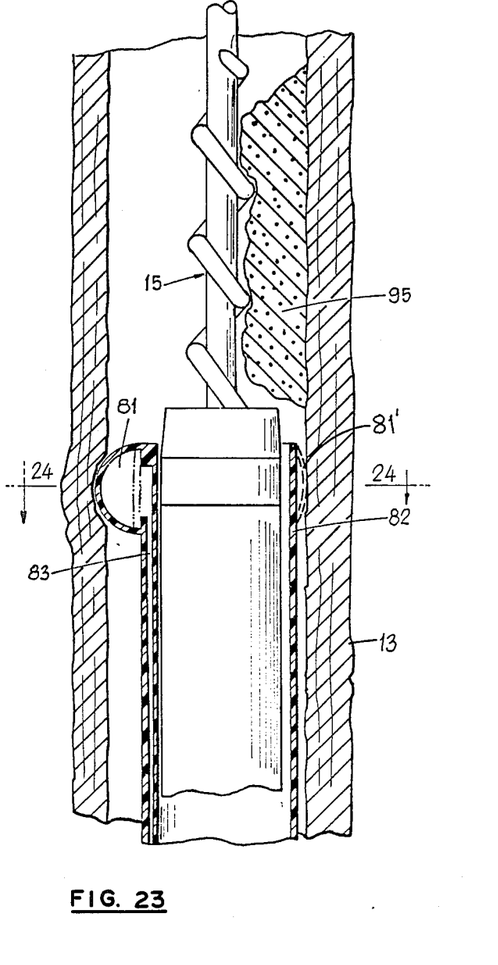
FIG. 23 shows a cross sectioned view of an inflatable chamber located at the distal end of the flexible sleeve.
Figure 24:
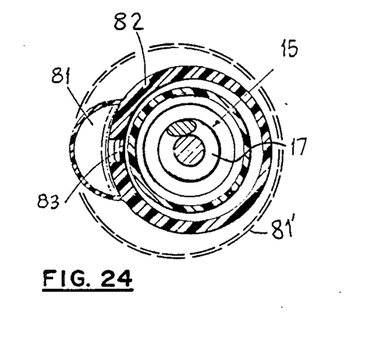
FIG. 24 shows a cross sectioned view of the chamber shown in FIG. 23 along a line 24—24 marked on FIG. 23.

FIGS. 23 and 24 show an alternative biasing means in the form of a dome shaped asymmetrical inflatable chamber 81 formed at the distal end of a flexible sleeve 82 which, when inflated through a channel 83 formed in the sleeve's wall, bears against the vessel's wall, as shown in solid lines, eccentrically biasing the flexible sleeve and the rotary coring means. When deflated, as shown in phantom lines, it wraps the sleeve to minimize interference with its insertion into the vessel. An alternate asymmetrical toroidal shaped inflatable chamber 81' is shown in an interrupted lines. This chamber, when inflated, establishes a peripheral contact with the arterial wall and thereby blocking blood flow between the sleeve and the arterial wall, as well as eccentricaly biasing the sleeve. It can be understood that a symmetrical toroidal chamber can be provided for the purpose of blocking the flow around the sleeve (without eccentrically biasing the sleeve). Any of the above mentioned chambers can also be inserted into the lumen that has been cored by the rotary coring means, to be inflated therein, and to further widen the lumen, however, such a procedure has some of the drawbacks of angioplasty.

Figure 25:
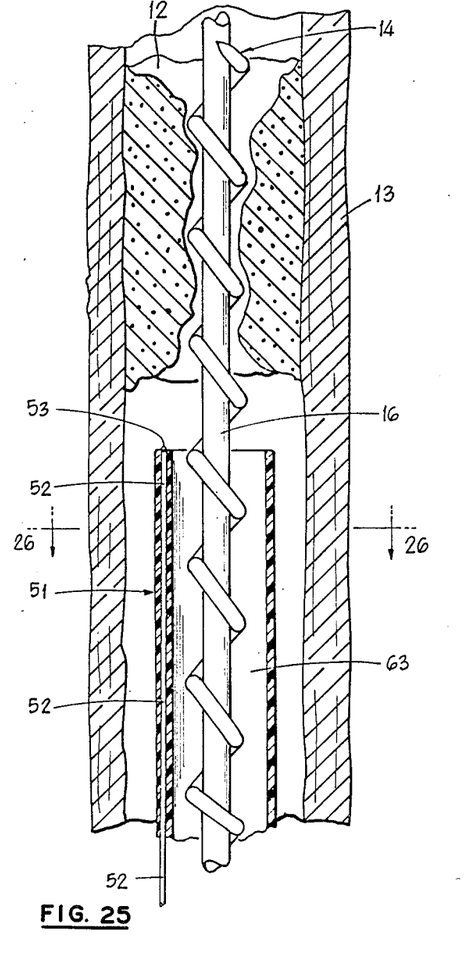
FIG. 25 shows a cross sectioned view of an atherectomy system where the rotary coring means utilizes a radiation emitting device.
Figure 26:
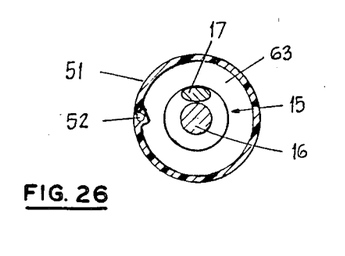
FIG. 26 shows a cross sectioned view of the system shown in FIG. 25 along a line 26—26 marked on FIG. 25.

FIGS. 25 and 26 show an atherectomy system having a flexible rotary-catheter 51 where the rotary coring means is a radiation emitting device in the form of an optical fiber (or fibers) 52 which emits laser energy through a lens 53 aligned with the distal end of the fiber. The laser energy cores the obstruction by cutting a narrow channel in it and the continuous passage 63 ingests the cored obstruction material as in previous embodiments. Similarly to the tubular-blade, the laser based rotary coring means is efficient and uses less energy in comparison to other laser based systems which pulverize the mass of the material of the obstruction. Using the same hypothetical obstruction which was used in the previous numerical example (having an outside diameter of 3 mm, an inside diameter of 1 mm and a length of 10 mm) with the system shown in FIG. 25, when laser energy is used to make a 0.1 mm wide peripheral cut, it has to disintegrate 9.42 cubic mm of material which is 15% of the obstruction's volume. The flexible rotary-catheter 51 can be rotateably disposed in any of the sleeves shown in connection to the previous embodiments. By using a sleeve equipped with a toroidal chamber to block blood flow as explained above and by introducing fluid, saline solution for example, through the sleeve or the flexible rotary-catheter, a working medium of choice can be created to suite a specific type of laser and to allow visual or spectroscopic analysis of the arterial lumen.

Figure 3:
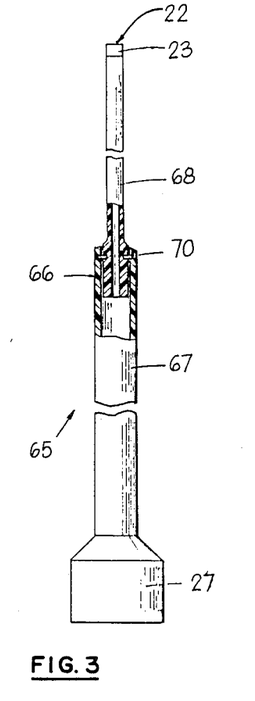
FIG. 3 shows a cross sectioned view of a flexible rotary-catheter equipped with a torque limiting clutch between its proximal end portion and distal end portion.

Torque generated by the motor is partially dissipated by frictional losses along the flexible rotary-catheter, therefore, the flexible rotary-catheter can be manufactured with a variable cross section, for example, an increased outside diameter and or/wall thickness at the vicinity of its proximal end compared with the same at its distal end, as shown in FIG. 2. This gives the flexible rotary-catheter an increased torque carrying capacity in the vicinity of its proximal end. Such a design is useful when treating small arteries in the heart or brain while entering the arterial system at the groin area as shown in FIG. 1, which requires a long flexible rotary-catheter having a distal end portion as small as 1 mm. As shown in FIG. 3 the flexible rotary-catheter 65 can be equipped with a torque limiting clutch 66 between the proximal and distal sections, 67 and 68, respectively, of the flexible rotary-catheter. The clutch is made by press fitting the section 68 into section 67 to establish frictional engagement between the two which limits the torque capacity of the clutch 66 to a certain permissible value, thereby protecting the smaller distal end from damage by occasional transfer of higher torques that may be applied at the proximal end. A lock-ring 70 prevents relative longitudinal displacement between sections 67 and 68 while not interfering with their relative rotation.

Referring back to FIG. 2, a flexible sleeve 71 in which the flexible rotary-catheter is rotatably disposed protects the arterial wall from the rotating catheter, and can be used to introduce the flexible rotary-catheter into the vessel. Means for introducing fluids into the vessel are connected to the flexible sleeve in the form of a nipple 72 leading into an annular chamber 73 which communicates with the sleeve. The annular chamber is equipped with a seal 74 which seals around the flexible rotary-catheter and forces fluid entering the nipple 72 to continue and move distally in the sleeve around the flexible rotary-catheter.

The atherectomy system can be manufactured in different diameters and lengths depending on the size and site of artery that it is intended for and on whether the system is to be used percutaneously (that is through the skin) or intra-operatively (that is when the vessel is surgically exposed for inserting the system into the vessel).

It can be noted from the FIGURES that the basic components of the atherectomy system can accept several optional features: The flexible rotary-catheter can be made from plastic or metal and either version can be equipped with a helical step. The rotary coring means can vary. The flexible guide-wire can be equipped with anti-rotational means, a distal barrier or an auger. The sleeve can be equipped with mechanical or hydraulic biasing and flow blocking means. By combining a flexible rotary-catheter with certain added features, a flexible guide-wire with certain added features and a sleeve with a certain added features a variety of species can be made. This increases the user's ability to match the system's characteristics with the specific condition that is treated, which is helpful, since the clinical characteristics of arterial atherosclerotic obstructions vary in geometry, hardness, and accessibility.

OPERATION

A process for removing an obstruction from a vessel with an atherectomy system, comprises the following steps:

Conventionally inserting into a vessel, into an obstruction, a flexible guide-wire. In case of a tight obstruction, an auger shaped flexible guide-wire can be rotated backwards so that the auger section will screw itself through the obstruction.

Advancing over the flexible guide-wire a rotary coring means located at a distal end of an atherectomy catheter.

Advancing the rotary coring means to the obstruction and coring the obstruction. During the operation the flexible guide-wire and the flexible sleeve (if present) are prevented from being rotationally dragged by the rotary coring means. Fluid can be delivered to the obstruction site through the flexible sleeve, around the atherectomy catheter. Such fluid can lubricate and cool the coring process and provide a medium for flushing particles of obstruction material into the atherectomy catheter, especially in conjunction with suction applied to the proximal end of the atherectomy catheter. The fluid may be radio-opaque to assist x-raying the process. Prior to coring, fluid can also be delivered through the atherectomy catheter.

Relative motion between the rotary coring means and the flexible guide-wire acting mechanically on the cored obstruction material enabling it to move proximally into a continuous passage defined in the atherectomy catheter and around the flexible guide-wire.

Removing the catheter containing the obstruction material out of the vessel.

The sequence of insertion of the components into the artery may vary depending on the nature and the location of the obstruction and the preferences of the medical staff. Additional steps may be added to assist the process. A standard guiding catheter, which is either straight or pre-formed, may function as a sleeve and be inserted into the vessel to assist in placing the flexible-guide-wire and the atherectomy catheter in the obstruction site.

When an arterial obstruction is further blocked by a fresh blood clot, as is often the case in a heart attack, the flexible guide-wire can usually be inserted through the clot and the atherectomy system can be used to first clear the clot, preferably while employing suction, and then to continue and core the underlying atherosclorotic obstruction. Therefore, the atherectomy system can be an effective tool in treating a heart attack, where the treatment will relieve the immediate threat to the patient's life and continue to provide a long term correction to the condition that induced the attack.

Differing strategies can be employed when dealing with the process of opening an arterial obstruction. A rotary coring means having an opening approximately equal in area to the artery's internal area can be chosen. This provides a good hydrodynamic result, however it raises the probability of injuring the artery or of leaving a thin layer of obstruction material hanging on the arterial wall. Such a thin layer which has no structural integrity of its own may fully or partially separate from the arterial wall and block the artery.

An alternative strategy is to choose a rotary coring means with an area of less than three quarters but more than one half the area of the unobstructed arterial lumen since the lower limit of this range is often sufficient to relief a patient's symptoms and the upper limit still leaves sufficient material to maintain the structural integrity of the obstruction reducing the likelihood of creating a flap, or of injuring the arterial wall even when dealing with an eccentric obstruction. After the obstruction is cored it is possible to further increase the lumen by angioplasty, however, this will introduce some of the undesirable side effects that are associated with angioplasty. Therefore, the choice of strategy will depend on the patient's specific disease characteristics and the judgement of the medical staff.

While the present invention has been illustrated by a limited number of embodiments, it should be understood that various modifications and substitutions may be made without departing from the spirit of the invention or the scope of the claims.

I claim:

1. An atherectomy system for coring, ingesting and removing an obstruction from within a patient's vessel, comprising in combination:
    a flexible guide-wire insertable into the vessel,
    a flexible rotary catheter, rotatably disposed and insertable into the vessel over said flexible guide-wire, having at its distal end a rotary coring means for making a circular cut in an obstruction located in front of it, and coupling means at its proximal end,
    a continuous passage, for ingesting the cored obstruction material, defined between said flexible rotary catheter and said flexible guide-wire, where the relative motion between said flexible rotary catheter and said flexible guide-wire assists in moving said ingested obstruction material proximally in said continuous passage, and,
    a rotating means having a hollow shaft connected to said proximal end through said coupling means, said hollow shaft being rotatable and slideable over said flexible guide-wire.

2. An atherectomy system as in claim 1, wherein suction is applied at said proximal end of said continuous passage to pull the cored obstruction material proximally in said continuous passage.

3. An atherectomy system as in claim 1, wherein a helical step formed on said rotating inner-wall mechanically acts on the cored obstruction material in said continuous passage, pushing it in a proximal direction.

4. An atherectomy system as in claim 3, said flexible guide-wire having anti-rotational means to counter rotation of the obstruction material around said flexible guide-wire while said rotary coring means cores the obstruction material and said helical step pushes the ingested obstruction material proximally.

5. An atherectomy system as in claim 4, wherein said anti-rotational means comprise at least one elongated radially protruding ridge.

6. An atherectomy system as in claim 5, wherein said protrusion of said elongated radially protruding ridge is selectively controlled.

7. An atherectomy system as in claim 6, wherein anti-rotational means comprise an expandable tube with at least one elongated ridge on its periphery.

8. An atherectomy system as in claim 1, said rotary coring means being a tubular-blade.

9. An atherectomy system as in claim 1, said rotary coring means being a variable diameter tubular-blade.

10. An atherectomy system as in claim 1, said rotary coring means being a heated tubular-blade.

11. An atherectomy system as in claim 1, said rotary coring means being a radiation emitting device.

12. An atherectomy system as in claim 1, at least a part of said flexible guide-wire having distal barrier means, extending radially from said flexible guide-wire, to counter distal movement of surrounding obstruction material while said rotary coring means core the obstruction material and said continuous passage ingests the obstruction material.

13. An atherectomy system as in claim 12, wherein said distal barrier means can elastically contract to pass through a narrowed lumen.

14. An atherectomy system as in claim 12, wherein said distal barrier means can be selectively contracted to pass through a narrowed lumen.

15. An atherectomy system as in claim 1, wherein said flexible rotary-catheter has a higher torque carrying capacity in the vicinity of said proximal end than in the vicinity of said distal end.

16. An atherectomy system as in claim 1, wherein said flexible rotary-catheter has a torque limiting clutch between said proximal end section to said distal end section.

17. An atherectomy system as in claim 1, having a flexible sleeve in which said flexible rotary-catheter is rotatably disposed.

18. An atherectomy system as in claim 17, said flexible sleeve having a biasing means for eccentrically biasing said flexible sleeve in the vessel.

19. An atherectomy system as in claim 18, said biasing means comprise an asymmetrical inflatable chamber formed at said distal end of said flexible sleeve.

20. An atherectomy system as in claim 18, said flexible sleeve having a tongue at its distal end for eccentrically biasing said flexible sleeve in the vessel.

21. An atherectomy system as in claim 20, said tongue being selectively actuatable.

22. An atherectomy system as in claim 17, wherein means for introducing fluids into the vessel are connected to said flexible sleeve.

23. An atherectomy system as in claim 1, wherein said flexible rotary-catheter comprises a helical member.

24. An atherectomy system as in claim 23, wherein said helical member has a helical surface which pushes the cored obstruction material in said continuous passage in a proximal direction.

25. An atherectomy system as in claim 23, wherein said helical member is disposed in a diametrically restraining member in the form of a flexible tube.

26. An atherectomy system as in claim 23, wherein said flexible rotary-catheter is disposed in a diametrically restraining member in the form of a helically wound member.

27. A process for removing an obstruction from an vessel with an atherectomy system, comprising the following steps:
   inserting into a vessel, into an obstruction, a flexible guide-wire,
   advancing over the flexible guide-wire a rotary coring means located at a distal end of an atherectomy catheter,
   advancing and rotating the rotary coring means to the obstruction and coring the obstruction,
   mechanically enabling the cored material to move proximally in a continuous passage defined between the atherectomy catheter and the flexible guide-wire,
   removing the atherectomy system containing the obstruction material out of the vessel.

28. A process as in claim 27, wherein suction is used in the continuous passage to assist the mechanical action in moving the cored obstruction material proximally.

* * * * *